(12) United States Patent
Hendriks et al.

(10) Patent No.: US 8,244,078 B2
(45) Date of Patent: Aug. 14, 2012

(54) HYDROGEL BASED SENSOR PROBE FOR DETECTING AN ENVIRONMENTAL STATE

(75) Inventors: Bernardus Hendrikus Wilhelmus Hendriks, Eindhoven (NL); Szabolcs Deladi, Eindhoven (NL); Ralph Kurt, Eindhoven (NL); Jan Frederik Suijver, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 233 days.

(21) Appl. No.: 12/600,881

(22) PCT Filed: May 22, 2008

(86) PCT No.: PCT/IB2008/052019
§ 371 (c)(1),
(2), (4) Date: Nov. 19, 2009

(87) PCT Pub. No.: WO2008/146212
PCT Pub. Date: Dec. 4, 2008

(65) Prior Publication Data
US 2010/0162834 A1 Jul. 1, 2010

(30) Foreign Application Priority Data
May 29, 2007 (EP) .................................. 07109095

(51) Int. Cl.
*G02B 6/00* (2006.01)

(52) U.S. Cl. ........ 385/12; 385/13; 250/227.19; 356/477

(58) Field of Classification Search ........................ None
See application file for complete search history.

(56) References Cited

U.S. PATENT DOCUMENTS

| 4,749,856 | A | 6/1988 | Walker et al. | |
| 4,778,987 | A * | 10/1988 | Saaski et al. | 250/226 |
| 5,015,843 | A | 5/1991 | Seitz et al. | |
| 5,611,998 | A | 3/1997 | Aussenegg et al. | |
| 6,590,665 | B2 * | 7/2003 | Painchaud et al. | 356/480 |
| 6,671,055 | B1 * | 12/2003 | Wavering et al. | 356/478 |
| 2002/0155425 | A1 | 10/2002 | Han et al. | |

(Continued)

FOREIGN PATENT DOCUMENTS
WO 03034047 A2 4/2003
(Continued)

OTHER PUBLICATIONS

Shakhsher et al: "Single Fiber-Optic pH Sensor Based on Changes in Reflection Accompanying Polymer Swelling"; Analytical Chemistry, vol. 66, No. 10, May 2004, pp. 1731-1735.
Seitz: "New Directions in Fiber Optic Chemical Sensors: Sensors Based on Polymer Swelling"; Journal of Molecular Structure, vol. 292, 1993, pp. 105-113.

(Continued)

*Primary Examiner* — Mike Stahl (57) ABSTRACT

A sensor probe for detecting an environmental state within a bodily lumen includes an elongated body having an optical guide with an outcoupling surface, which is part of an end surface of the elongated body, facing a reflective surface of an overhanging part. The sensor probe further includes a photodetector which detects a property of light which is composed of light in the optical guide that is reflected from the outcoupling surface of the optical guide and of light in the optical guide that is reflected from the overhanging part. The sensor probe also includes a hydrogel material having a property that changes when getting into contact with an environmental material and/or when detecting an environmental change. The hydrogel material is provided between the end surface of the elongated body and the overhanging part.

8 Claims, 11 Drawing Sheets

U.S. PATENT DOCUMENTS

2002/0162399 A1* 11/2002 Esashi et al. .................. 73/715
2003/0112443 A1* 6/2003 Hjelme et al. ................ 356/480
2005/0265649 A1 12/2005 da Silva, Jr. et al.
2008/0159687 A1* 7/2008 Donlagic et al. ............... 385/13

FOREIGN PATENT DOCUMENTS

WO    2008044186 A2    4/2008

OTHER PUBLICATIONS

Schalkhammer et al: "The Use of Metal-Island-Coated pH-Sensitive Swelling Polymers for Biosensor Applications"; Sensors and Actuators B, vol. 24, No. 1-3, pp. 166-172, (1995).

Aussenegg et al: "The Metal Island Coated Swelling Polymer Over Mirror System (MICSPOMS): A New Principle for Measuring Ionic Strength"; Sensors and Actuators B, vol. 29,, No. 1 Oct. 1995, pp. 204-209.

Kim et al: "Label-Free Biosensing With Hydrogel Microlenses"; Angew. Chem. Int. Ed., 2006, vol. 45, pp. 1446-1449.

Hilt et al: "A BioMEMS Sensor Platform Based on a Cantilever With a Precisely Patterned Environmentally Sensitive Hydrogel"; Proceedings of the Seond Joint EMBS/BMES Conference, Houston, TX, Oct. 23-26, 2002, pp. 1650-1651.

Lei et al: "An Ultrasensitive Chemical Microsensor Based on Self-Aligned Dry-Patterned Environmentally Sensitive Hydrogels"; Transducers '05, The 13th Conference on Solid-State Sensors, Actuators and Microsystems, Seoul, Korea, Jun. 5-9, 2005, pp. 1824-1827.

Miyata et al: "A Reversibly Antigen-Responsive Hydrogel"; Letters to Nature, 1999 MacMillan Magazines Ltd., Nature vol. 399, pp. 766-769.

\* cited by examiner

HYDROGEL BASED SENSOR PROBE FOR DETECTING AN ENVIRONMENTAL STATE

FIELD OF THE INVENTION

The invention relates to a sensor probe with a stimuli-sensitive hydrogel material for detecting an environmental state.

BACKGROUND OF THE INVENTION

Stimuli-sensitive hydrogels have found applications in actuators, sensors, drug delivery and bio separations. These materials are able to respond reversibly to an external stimulus that causes a distinct measurable effect on the physical properties of the material. Hydrogels are known to be sensitive to pH, ion concentration, temperature, solvent composition and electric potential. The hydrogels can be also designed to swell upon presence of a target molecule. They can be constructed in a way that the magnitude of swelling can be proportional to the concentration of ligands being present.

Minimal invasive procedures are characterized in that either through natural openings of the body or through tiny incisions inspection of the interior of the human or animal body is executed with devices such as an endoscope and a catheter. Important parameters to be measured in the human or animal body are temperature and pH level, because these are strong indicators for diseased tissue. Moreover biomarkers such as enzymes, proteins, cytokines, sugar derivates (such as e.g. glucose) and other small molecules can further help to characterize the state of the tissue.

In "An ultrasensitive chemical microsensor based on self-aligned dry-patterned environmentally sensitive hydrogels" by M Lei et al., Proc. 13th Int. Conf. Solid state sensors, actuators and microsystems, Korea, 2005, pp 1824-1827 an ultrasensitive chemical microsensor based on an environmentally sensitive hydrogel actuated cantilever beam is disclosed. The hydrogel swells in response to an increase of pH or glucose concentration and lifts and deflects the cantilever. The deflection can be detected with a variety of sensing techniques, such as optical, piezo-resistive or piezo-electric techniques. A disadvantage of the known sensor is that it is not suitable for application inside a bodily lumen, because it is not biocompatible, it is provided on a silicon substrate and it requires a separate system to detect the deflection of the cantilever.

SUMMARY OF THE INVENTION

It is an object of the invention to provide a compact sensor probe for detecting an environmental state within a bodily lumen. The invention is defined by the independent claims. Advantageous embodiments are defined by the dependent claims.

This object is achieved by the sensor probe for detecting an environmental state within a bodily lumen according to the invention, which comprises an elongated body comprising an optical guide having an outcoupling surface at a first end of the elongated body facing a reflective surface of an overhanging part, a photodetector which detects a property of light which is composed of light in the optical guide that is reflected from the outcoupling surface of the optical guide and of light in the optical guide that is reflected from the overhanging part, and a hydrogel material of which a property changes when getting into contact with an environmental material and/or when detecting an environmental change, and which is provided between the first end of the elongated body and the overhanging part. In this way a sensor probe is provided that, because of its compactness, can be applied inside the bodily lumen for detecting and characterizing parameters that are vital indicators for the state of the human or animal body, and to which the hydrogel material is responsive, such as, for example, temperature or pH. As another example, the presence, absence or concentration of biomarkers inside the bodily lumen can be measured by applying a hydrogel material, which comprises biomarker binding sites and, hence, is sensitive to a dedicated biomarker. Another advantage is that the optical detection system, comprising the optical waveguide and the photodetector, is integrated into the sensor probe, thus making it an even more compact device. The photodetector can, for example, detect the intensity and/or the phase of the light it receives. The measurement of the phase, comprising an interference pattern composed of the light reflected from the outcoupling surface of the optical guide and the light reflected from the flexible part of the opto-mechanical force transducer, results in a more accurate measurement, because the wavelength of light is the basis for the measurement, which is a parameter that results in more accurate measurement results than the intensity of light.

In an embodiment of the sensor probe according to the invention the overhanging part is flexible and the hydrogel material is adapted to change its volume when getting into contact with an environmental material and/or when detecting an environmental change, thereby deforming the flexible overhanging part. A change in volume of the hydrogel material displaces or deforms the flexible overhanging part resulting in a change of the property of the light that is detected by the photodetector. For example, a hydrogel material of which its volume is sensitive to temperature or pH may be used thereby providing for a sensor probe that is able to measure the temperature or pH inside a bodily lumen.

In an embodiment of the sensor probe according to the invention at least one end of the overhanging part is mounted on the first end of the elongated body and at least partially supported by the hydrogel material. In this way the hydrogel material advantageously both functions as a mounting means for the overhanging part onto the elongated body and as a detection means for detecting a change in the environmental state by displacing one end of the overhanging part upon swelling and thus bending the overhanging part because of the supporting function of the hydrogel material.

In an embodiment of the sensor probe according to the invention the overhanging part is a disc. This allows for the use of simple, cheap batch processing for the manufacturing of the overhanging part such as, for example, silicon MEMS (Micro Electro Mechanical Systems) fabrication techniques. Furthermore, the shape of the disc reduces the risk of damaging the interior of the human or animal body with respect to the use of, for example, a bridge-like structure comprising relatively sharp edges. In a further advantageous embodiment the hydrogel material is adapted to change its volume when getting into contact with an environmental material and/or when detecting an environmental change and the disc is supported and mounted on the first end of the elongated body supported by a ring-shaped support comprising the hydrogel material thereby forming a closed space region. In this way the hydrogel material both functions as a mounting means for the disc onto the elongated body and as a detection means for detecting a change in the environmental state by lifting or displacing the disc upon swelling of the hydrogel material.

In an embodiment of the sensor probe according to the invention the hydrogel material is adapted to change its optical properties when getting into contact with an environmental material and/or when detecting an environmental change, and in which the hydrogel material is provided in the path of light that is reflected from the overhanging part. A change in the optical properties of the hydrogel material results in a change of the property of the light that is detected by the photodetector, because part of that light has penetrated the hydrogel material. In this way no deformation or displacement takes place in the sensor probe, which makes the sensor probe more robust.

In an embodiment of the sensor probe according to the invention at least one end of the overhanging part is supported by a rigid support mounted on the first end of the elongated body outside of the outcoupling surface. The rigid support on one end of the flexible connection away from the outcoupling surface advantageously provides for a solid mounting of the overhanging part on the elongated body and in a well-defined relative position of the overhanging part in relation to the outcoupled surface of the optical guide without influencing the outcoupled and reflected light.

In an embodiment of the sensor probe according to the invention the overhanging part comprises a fiber material at least partly coated with a reflective material on the bottom surface or on the top surface of the overhanging part. This embodiment enables a simplified manufacturing of the sensor probe by using, for example, the same material for the optical guide and the overhanging part such as an optical fiber material. By adding a reflective coating on one of the surfaces of the overhanging part, the intensity of the reflected light is increased resulting in a more accurate measurement of the reflected light by the photodetector. Examples of reflective material include Pt, Ag and Au.

In an embodiment of the sensor probe according to the invention, the sensor probe further comprises processing logic for computing the environmental state from an output signal of the photodetector. The processing logic can also be present outside the sensor probe and a connection between the sensor probe and any external apparatus can be implemented via a wireless connection in which the sensor probe is adapted to be wirelessly connected to any external apparatus.

BRIEF DESCRIPTION OF THE DRAWINGS

These and other aspects of the invention will be further elucidated and described with reference to the drawings, in which.

The Figures are not drawn to scale. In general, identical components are denoted by the same reference numerals in the Figures.

DETAILED DESCRIPTION OF EMBODIMENTS

Stimuli-sensitive hydrogel materials have applications in actuators, sensors, drug delivery, bioseparations and biomedicine. These materials are able to respond reversibly to an external stimulus that causes a distinct measurable effect on the properties of the material. Hydrogel materials are known to be sensitive to pH, ion concentration, temperature, solvent composition and electric potential. These parameters cause a change in phase, shape, mechanics, refractive index, recognition or permeation rates that subsequently can be reversed to return the material to its original state. Stimuli-sensitive hydrogel materials have also been integrated with enzymes, protein mimics, and antibodies to design controllable actuators. These hydrogel materials have been shown to swell on addition of a target molecule. The amount of swelling of these hydrogel materials was attributed to changes in non-covalent interactions within the polymer network. The hydrogel materials can be also designed to swell upon presence of a target molecule. They can even be constructed in a way that the magnitude of swelling can be proportional to the concentration of target molecule present. Huge swelling ratios can be obtained, the materials are, for example, very sensitive to even small changes in pH. A typical pH sensitive hydrogel material is polyacrylic acid (PAA) and a typical temperature sensitive hydrogel material is N-isopropylacrylamide (NPA). Some stimuli-responsive hydrogel materials additionally undergo very abrupt changes in optical properties in response to external stimuli such as temperature. An example of this effect is known as lower critical solution temperature. In fact some hydrogel materials undergo a very sharp phase transition when increasing the temperature and change from an optically transparent material into a scattering material. The fact that the lower critical solution temperature of these hydrogel materials can be adjusted to near human body temperature (37° C.) by copolymerization and using additives further makes them viable for in-vivo applications. Furthermore, the use of water-based materials slows down the encapsulation process of a foreign body by the human immune system, which makes hydrogel materials extremely attractive as a base for implantable long lasting chemo-physical sensors. Hydrogel-based transducers therefore will lead to long lasting implantable sensing systems enabling accurate monitoring of physiological parameters outside of and/or within the human/animal body. The proposed transducer device makes use of the response of the hydrogel material to an environmental change (for example pH, temperature) or a specific molecule. In order to become sensitive to the presence of a specific molecule (analyte) the hydrogel should be "tailored" with specific "analyte-analyte binding molecules" complexes, for example antigen as analyte and an antibody as analyte binding molecule or carbohydrates as analyte and Lectins as analyte binding molecule.

Figure 1:
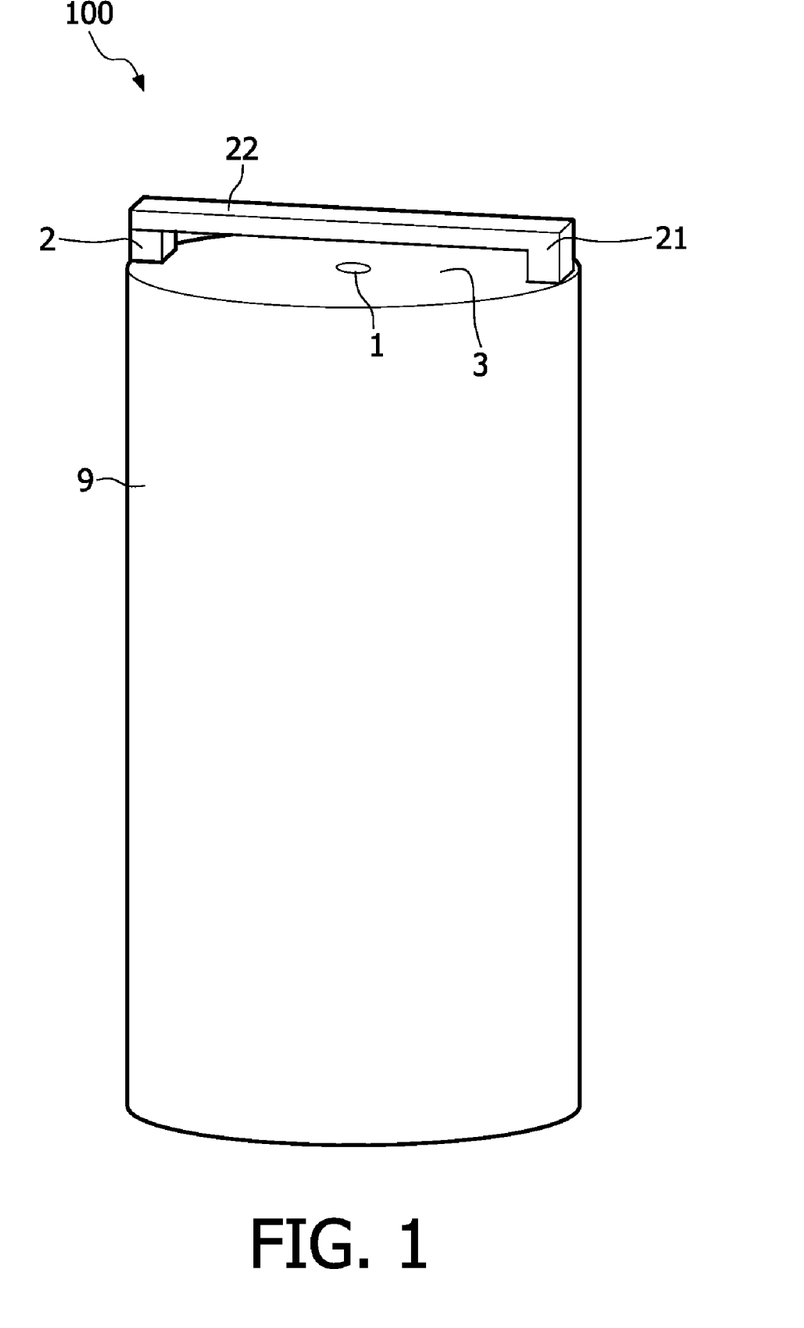
FIG. 1 is perspective view of an end part of a sensor probe according to an embodiment of the invention.

FIG. 1 shows a perspective view of an end part of a sensor probe 100 according to an embodiment of the invention. The sensor probe 100 is, for example, part of a catheter or an endoscope, or any apparatus used for diagnosis or treatment inside a bodily lumen. The end part of the sensor probe 100 as shown in FIG. 1 comprises an elongated body 9, such as, for example, a cylinder, with an end surface 3 and having an optical waveguide 1 in the middle for guiding light 30 originating from a laser source (not shown). The optical waveguide can, for example, be fabricated from a fiber material and be surrounded by a material with a refractive index that is different from that of the optical waveguide 1. The sensor probe 100 further comprises an overhanging structure with a flexible part 22 supported on one side by a rigid support 21 and on the opposite side by a stimuli-responsive hydrogel material 2, which, in this case, is adapted to increase its volume in response to, for example, a change in temperature or pH. Both the rigid support 21 and the hydrogel material 2 are mounted on the end surface 3 of the elongated body 9. The flexible part 22 is located in the path of light that exits from the optical waveguide 1.

The sensor probe 100 and the flexible part 22 can be fabricated directly from an optical fiber by, for example, focused ion beam milling or by a combination of lithographic techniques and reactive ion etching of the fiber, followed by patterning of the hydrogel material 2.

Figure 2:
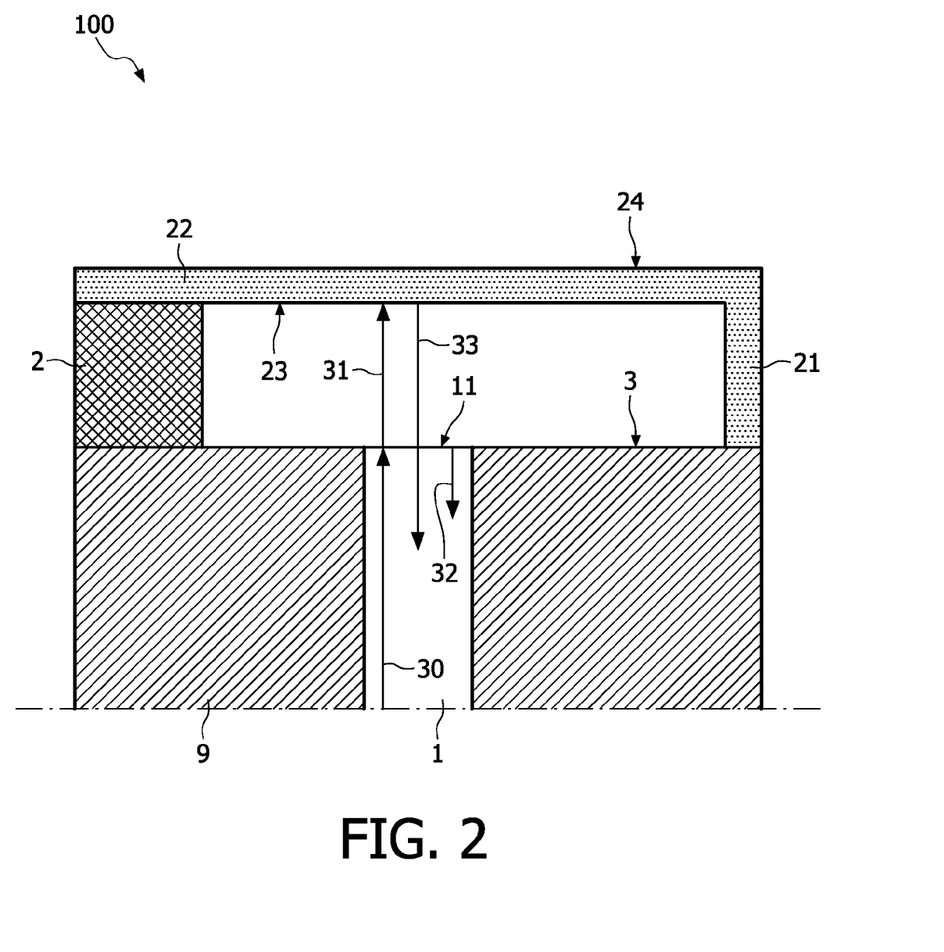
FIGS. 2 and 3 are cross-sectional views of an end part of a sensor probe according to an embodiment of the invention.
Figure 3:
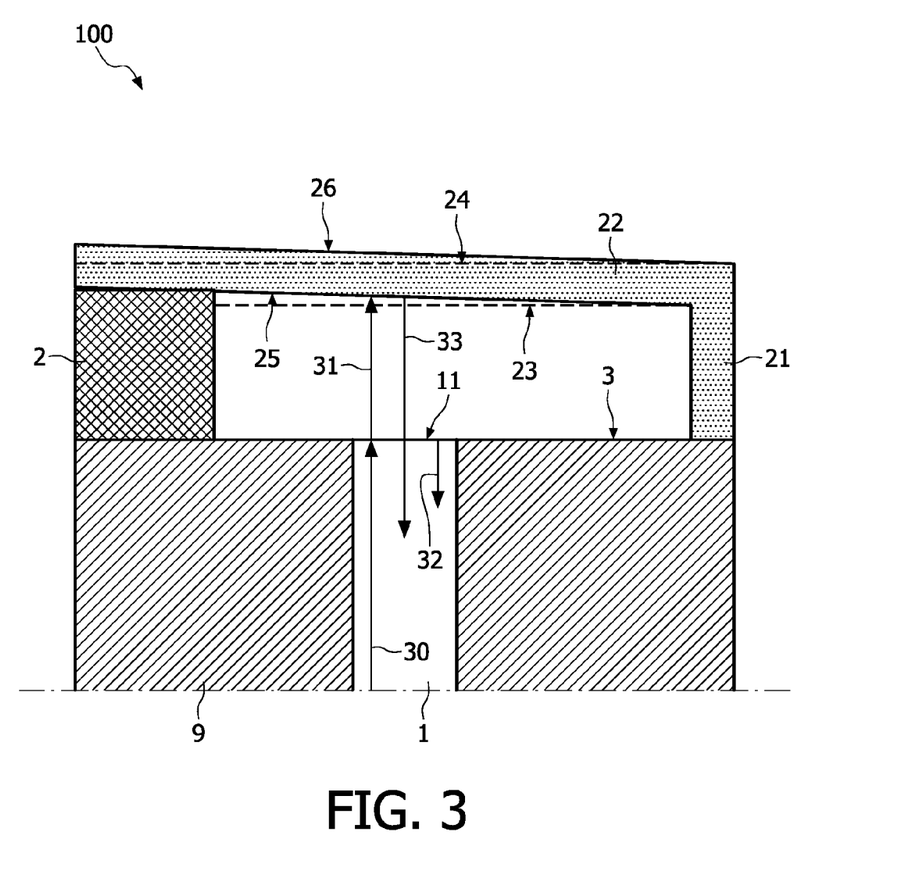

FIGS. 2 and 3 are cross-sectional views of the end part of the sensor probe 100 according to an embodiment of the invention and explain in more detail the operation of the sensor probe 100. The flexible part 22 comprises a bottom surface 23 that faces the outcoupling surface 11 and a top surface 24 opposite to the bottom surface 23. A first part 31 of the light 30 in the optical waveguide 1 that is originating from the laser source (not shown) exits from the optical waveguide 1 at an outcoupling surface 11, which is part of the end surface 3 of the elongated body 9. First reflected light 32 comprises a second part of the light 30 that is reflected at the outcoupling surface 11 and is guided in the opposite direction of the light 30 in the optical waveguide 1. Second reflected light 33 comprises a part of the first part 31 of the light 30 that is reflected at the bottom surface 23 of the flexible part 22 and that enters the optical waveguide 1 through the outcoupling surface 11. Hence, the optical waveguide 1 guides two light beams in a direction opposite to the direction of the light 30: the first reflected light 32, which is reflected from the outcoupling surface 11, and the second reflected light 33, which is reflected from the bottom surface 23 of the flexible part 22 and which entered the optical waveguide 1 through the outcoupling surface 11. These two reflected light beams 32 and 33 are combined in the optical waveguide and are detected at an end of the optical waveguide 1 that is opposite to the outcoupling surface 11 of the sensor probe 100 via, for example, a photodetector that will generate a voltage or current signal in dependence of, for example, the intensity and/or phase of the combined light. The measurement of the phase comprising an interference pattern composed of the first reflected light 32 and the second reflected light 33 results in a more accurate measurement, because the wavelength of light is the basis for this measurement, which is a parameter that results in more accurate measurement result than the measurement of the intensity of light.

FIG. 3 shows the sensor probe 100 after swelling of the hydrogel material 2. The swelling of the hydrogel material 2 forces the flexible part 22 to deform or bend, resulting in a displacement or deformation of the bottom surface 23 to the deformed bottom surface 25 and of the top surface 24 to the deformed top surface 26. As a result of the displacement of the flexible part 22, the distance between the outcoupling surface 11 and the flexible part 22 is changed from the bottom surface 23 to the deformed bottom surface 25. Hence the length of the path of the second reflected light 33 is changed, which results in a change of the properties of the combination of the first reflected light 32 and the second reflected light 33. This change of, for example, the intensity and/or phase is then measured with the photodetector, and converted into a value for the displacement of the flexible part 22. Because the characteristics of the flexible part 22, such as for example stiffness, and the sensitivity of the hydrogel material 2 to the change of, for example, temperature or pH are known, the value of the temperature or pH are computed in this way by, for example, processing logic circuitry. The characteristics of the flexible part 22 are designed such that the swelling of the hydrogel material 2 results in a deformation of the flexible part 22. For example, the flexible part will have a length of 40 micrometers, a width of 25 micrometers and a thickness of 20 micrometers. An embodiment of the flexible part 22 comprises, for example, silicon oxide, wherein the top surface 24 of the flexible part 22 is coated with a material that reflects light. Such a material is for example Pt or Au, and is at least applied on an area of the top surface 24 that is located above and facing the outcoupling surface 11. In this case, a part of the first part 31 of the light 30 will enter the flexible part 22 and will subsequently reflect from the top surface 24 and enter the optical waveguide 1. Furthermore, in this case the second reflected light 33 is only a fraction of the part of the first part 31 of the light 30 that enters the flexible part 22, for example only 4% reflects at the bottom surface 23 of the flexible part 22. Alternatively, a part of the bottom surface 23 of the flexible part 22 may be coated with the reflective material.

Figure 4:
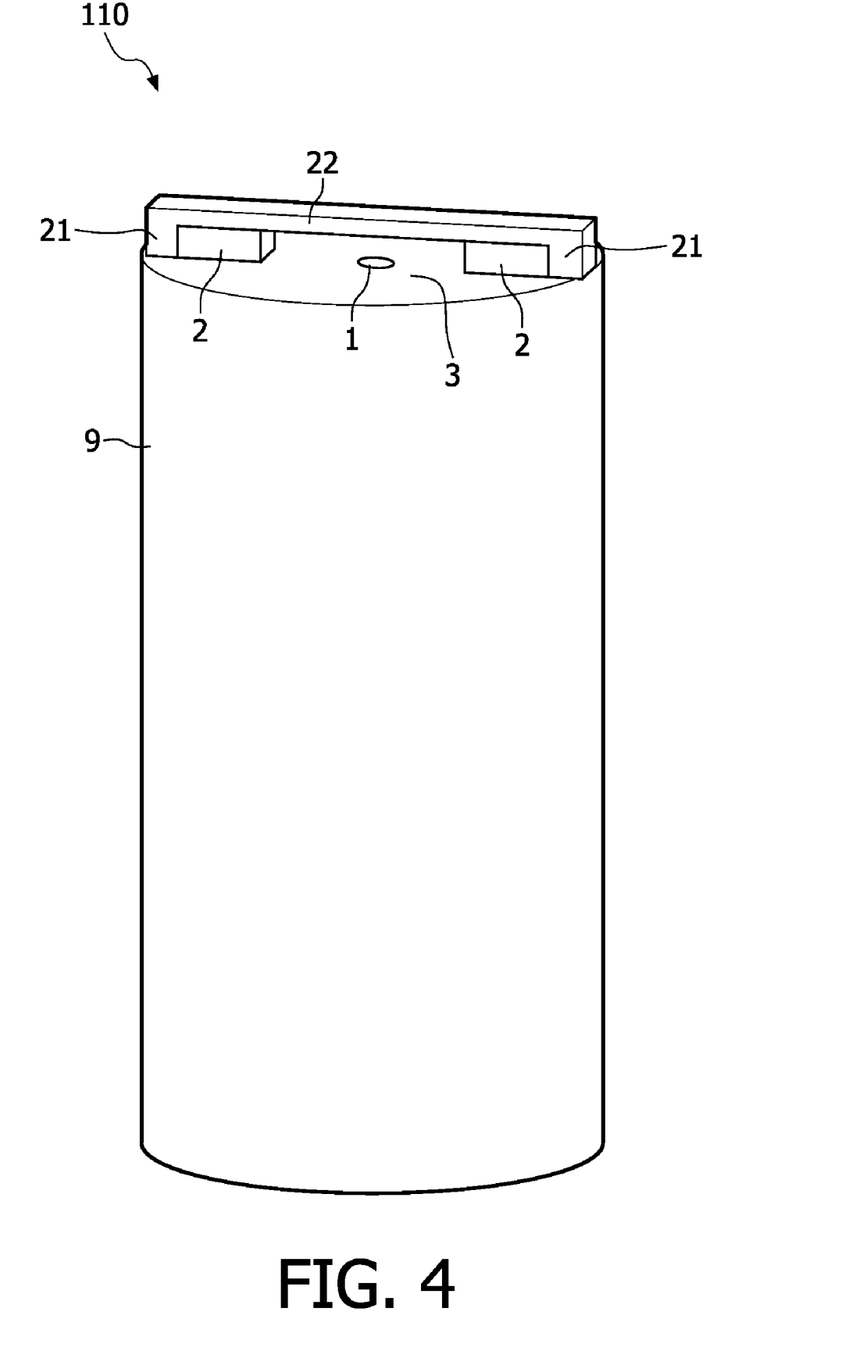
FIG. 4 is a perspective view of an end part of a sensor probe according to an embodiment of the invention.

FIG. 4 shows a perspective view of an end part of a sensor probe 110 according to an embodiment of the invention. The overhanging structure with the flexible part 22 is in this embodiment supported on two sides by the rigid support 21 mounted on the end surface 3 of the elongated body 9. The stimuli-responsive hydrogel material 2 is provided between, and adjoining, the flexible part 22 and the elongated body 9 and outside the path of light that exits from the optical waveguide 1. Also in this case the hydrogel material 2 is adapted to increase its volume in response to an environmental change such as, for example, a change in temperature or pH.

Figure 5:
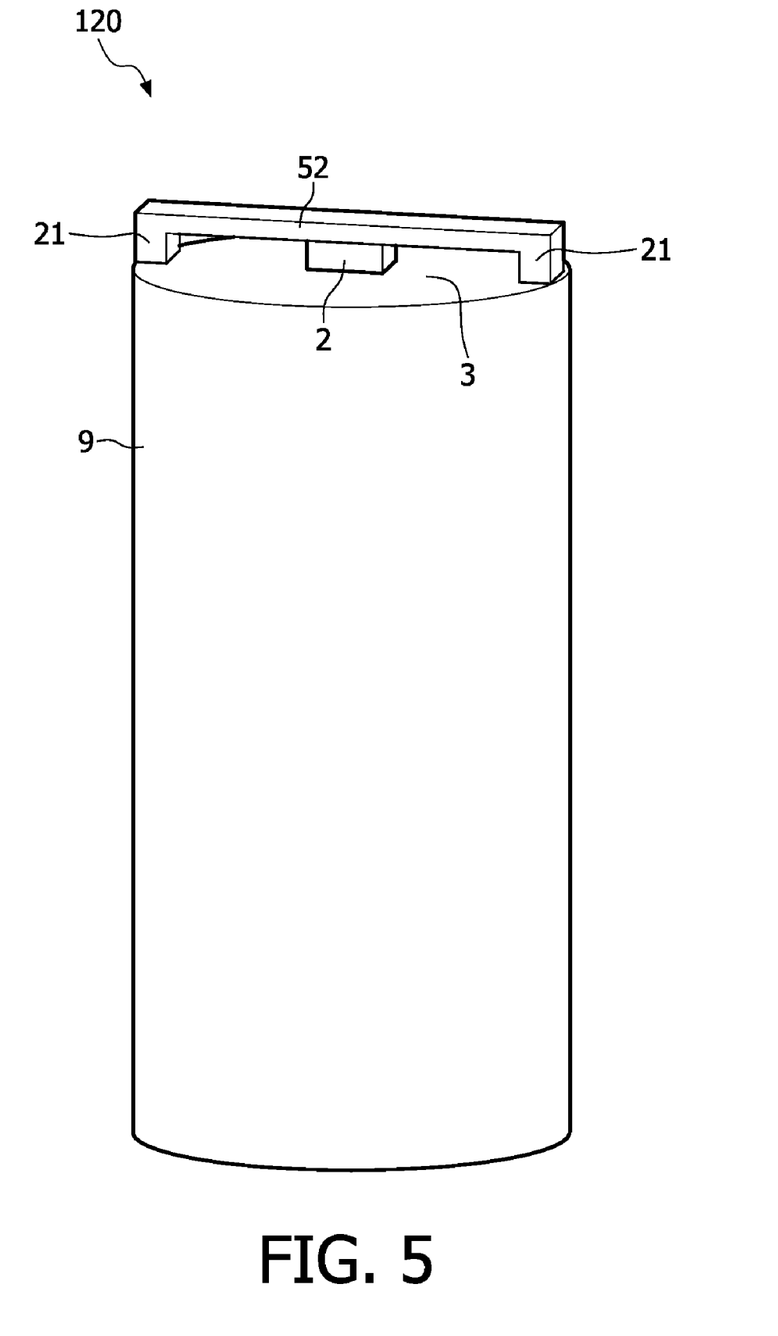
FIG. 5 is perspective view and FIG. 6 a cross-sectional view of an end part of a sensor probe according to an embodiment of the invention.

FIG. 5 shows a perspective view of an end part of a sensor probe 120 according to an embodiment of the invention. The overhanging structure in this embodiment does not necessarily have to be flexible, and comprises a rigid part 52 which is supported on two sides by the rigid support 21 mounted on the end surface 3 of the elongated body 9. The stimuli-responsive hydrogel material 2 is provided between, and adjoining, the rigid part 52 and the end surface 3 of the elongated body 9 in the path of light that exits from the optical waveguide 1. In this embodiment the optical properties of the hydrogel material 2 will change in response to an environmental change such as, for example, a change in temperature or pH.

Figure 6:
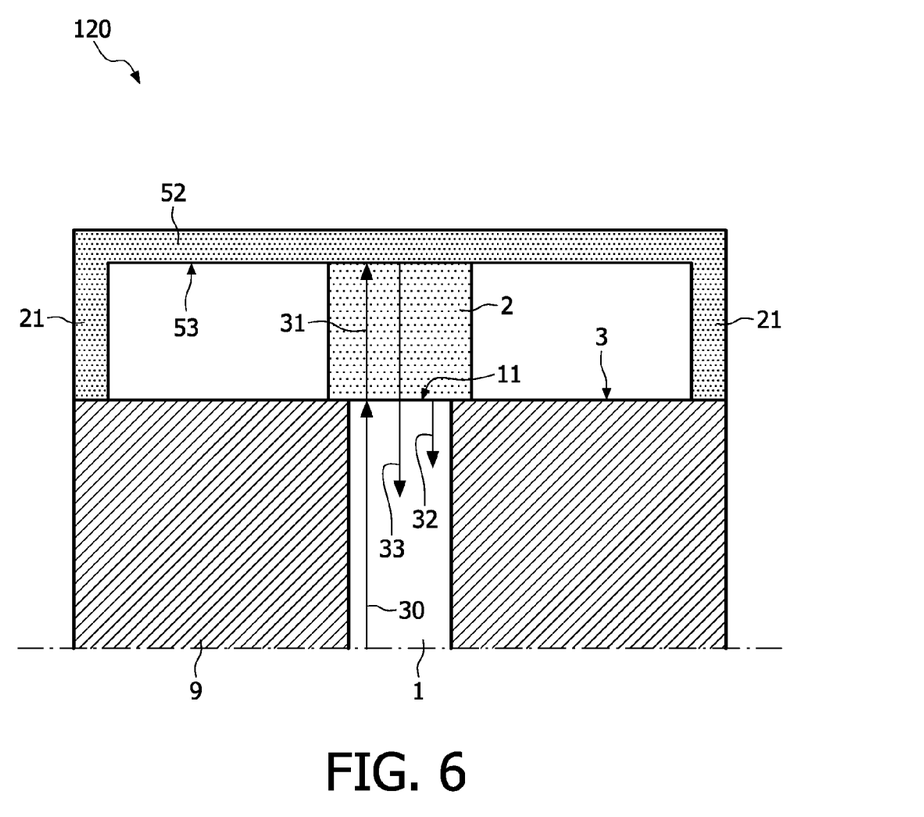

FIG. 6 is a cross-sectional view of the end part of the sensor probe 120 and explains in more detail the operation of the sensor probe 120. The first part 31 of the light 30 in the optical waveguide 1 that is originating from the laser source exits from the optical waveguide 1 at the outcoupling surface 11 and goes through the hydrogel material 2. Also the second reflected light 33, which is reflected at a bottom surface 53 of the rigid part 52, will go through the hydrogel material 2 before it enters the optical waveguide 1 through the outcoupling surface 11 (not shown). Hence, the changed optical properties of the hydrogel material 2 will influence the properties of the first part 31 of the light 30 and the second reflected light 33 and, hence, the resulting intensity and/or phase of the light detected by the photodetector will be affected by the changed optical properties of the hydrogel material 2. This change is a measure for the environmental change as is detected by the hydrogel material 2, for example the change in the temperature or pH.

Figure 7A:
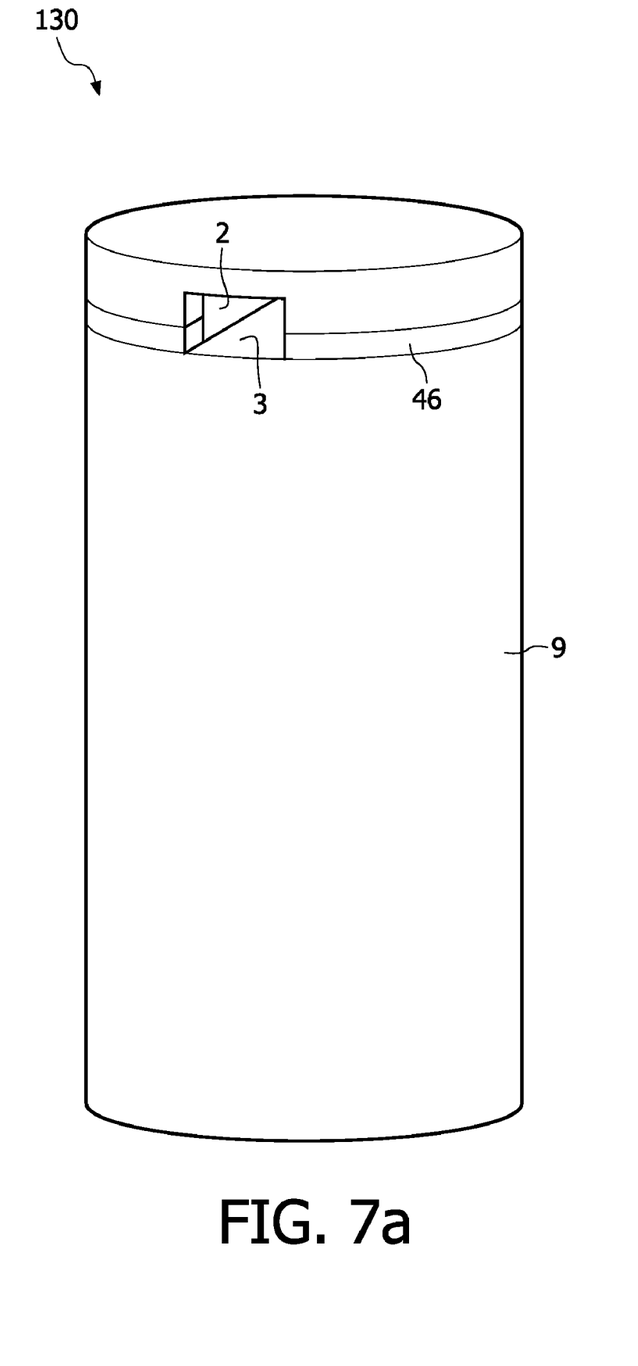
FIG. 7a is a perspective view and FIG. 7b a perspective cross-sectional view of an end part of a sensor probe according to an embodiment of the invention.
Figure 7B:
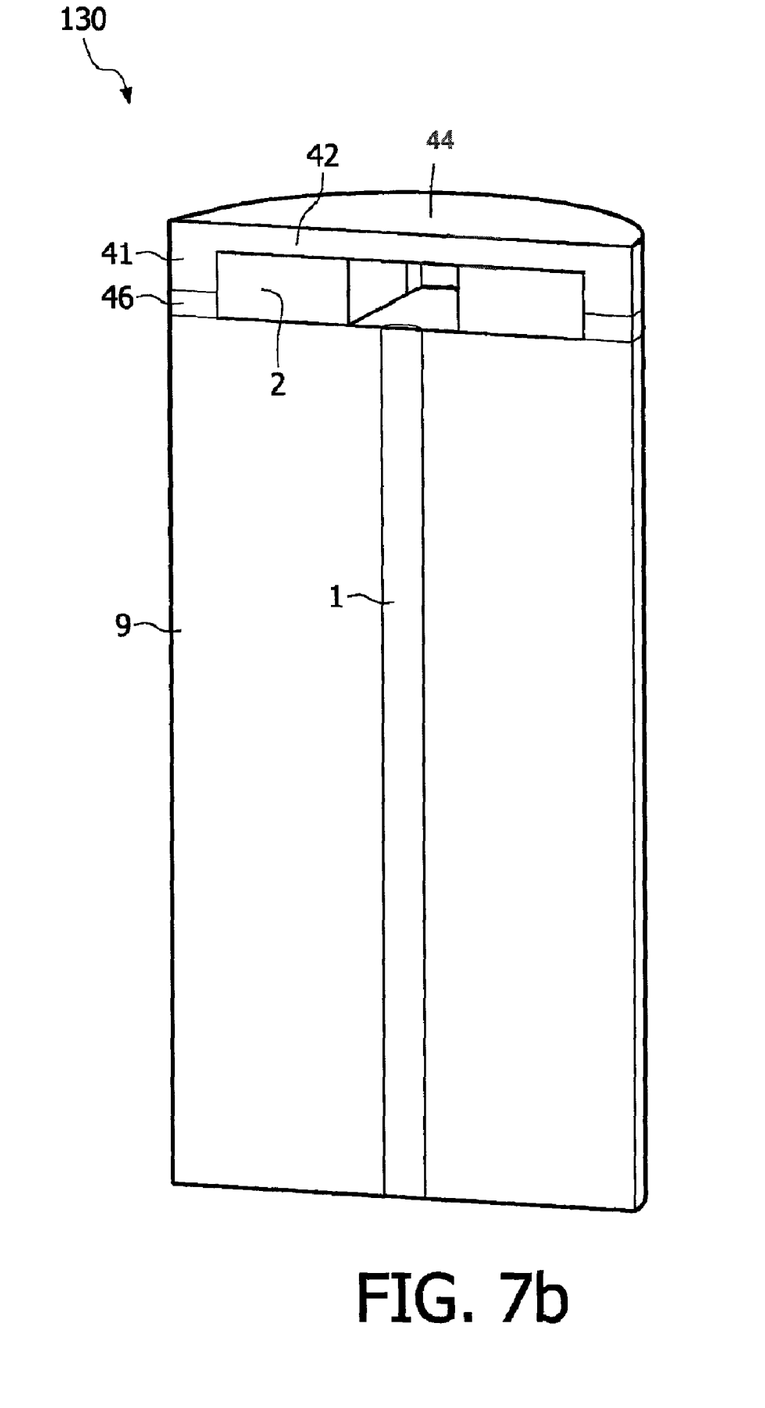

FIG. 7a shows a perspective view and FIG. 7b a perspective cross-sectional view of a sensor probe 130 according to another embodiment of the invention. In this case the flexible part of the sensor probe 130 is a flexible disc 42 having a top surface 44. The flexible disc 42 is supported and mounted via an auxiliary material, such as, for example, a glue layer 46, on the end surface 3 of the elongated body 9 by a rigid, partially ring-shaped, support 41. The stimuli-responsive hydrogel material 2 is provided between, and adjoining, the flexible disc 42 and the end surface 3 of the elongated body 9 and outside the path of light that exits from the optical waveguide 1. In this case the hydrogel material 2 is adapted to increase its volume in response to an environmental change such as, for example, a change in temperature or pH. The swelling of the hydrogel material 2 induces a deformation of the flexible disc which results in a change of, for example, the intensity and/or phase of the light detected by the photodetector. The sensor probe 130 may also be applied in an in-vivo flow cytometer where the properties of particles, such as red blood cells, are optically inspected in a flow channel.

The flexible disc 42 can be fabricated and provided on the hydrogel material 2 using Micro Electro Mechanical Systems (MEMS) technology, for example from silicon. In a second phase of the fabrication process the MEMS devices including the hydrogel material 2 and the rigid ring support 41 are aligned and mounted, for example with epoxy resin, onto the end of the elongated body 9. This fabrication is relatively cheap because batch processing may be applied.

Figure 8:
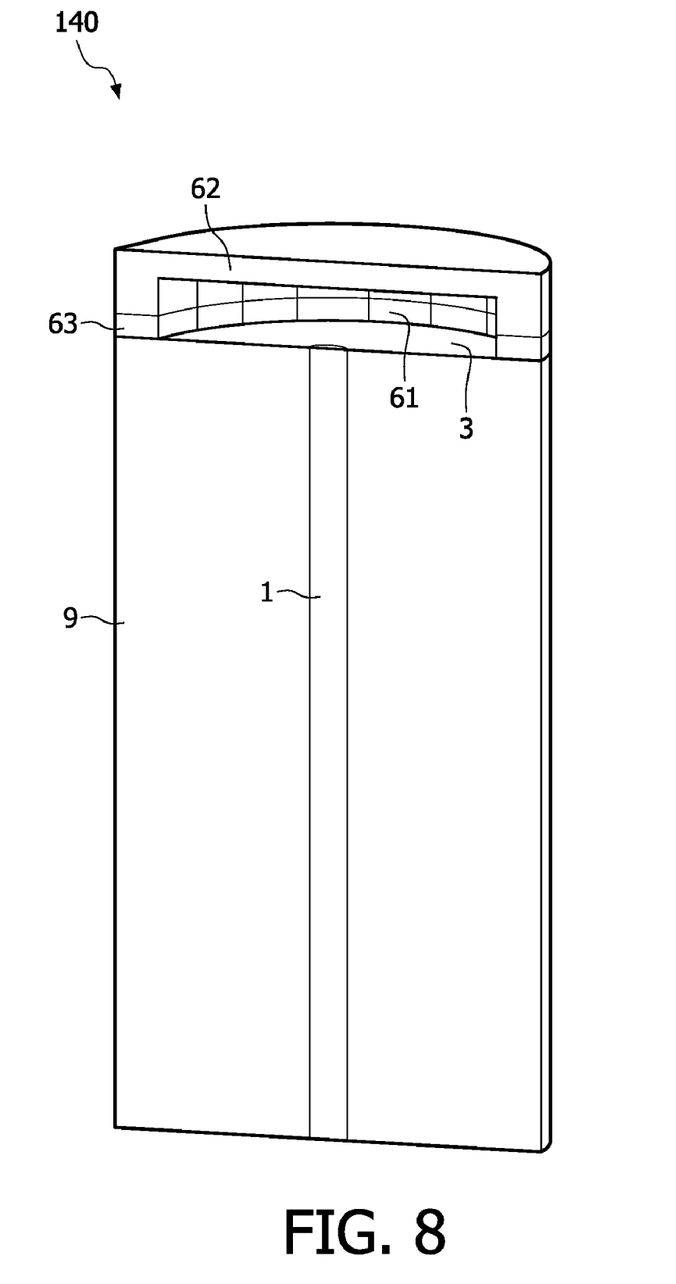
FIG. 8 is a perspective cross-sectional view of an end part of a sensor probe according to an embodiment of the invention.

FIG. 8 shows a perspective cross-sectional view of an end part of a sensor probe 140 according to an embodiment of the invention. The overhanging structure in this embodiment does not necessarily have to be flexible, and comprises a rigid disc 62 which is supported by a ring support 63 comprising the hydrogel material 2 mounted on the end surface 3 of the elongated body 9, thereby forming a cavity 61. The swelling of the hydrogel material 2, in this case, displaces the rigid disc 62 with respect to the elongated body 9 and thus results in a change of the, for example, intensity and/or phase of the light detected by the photodetector pattern.

Figure 9A:
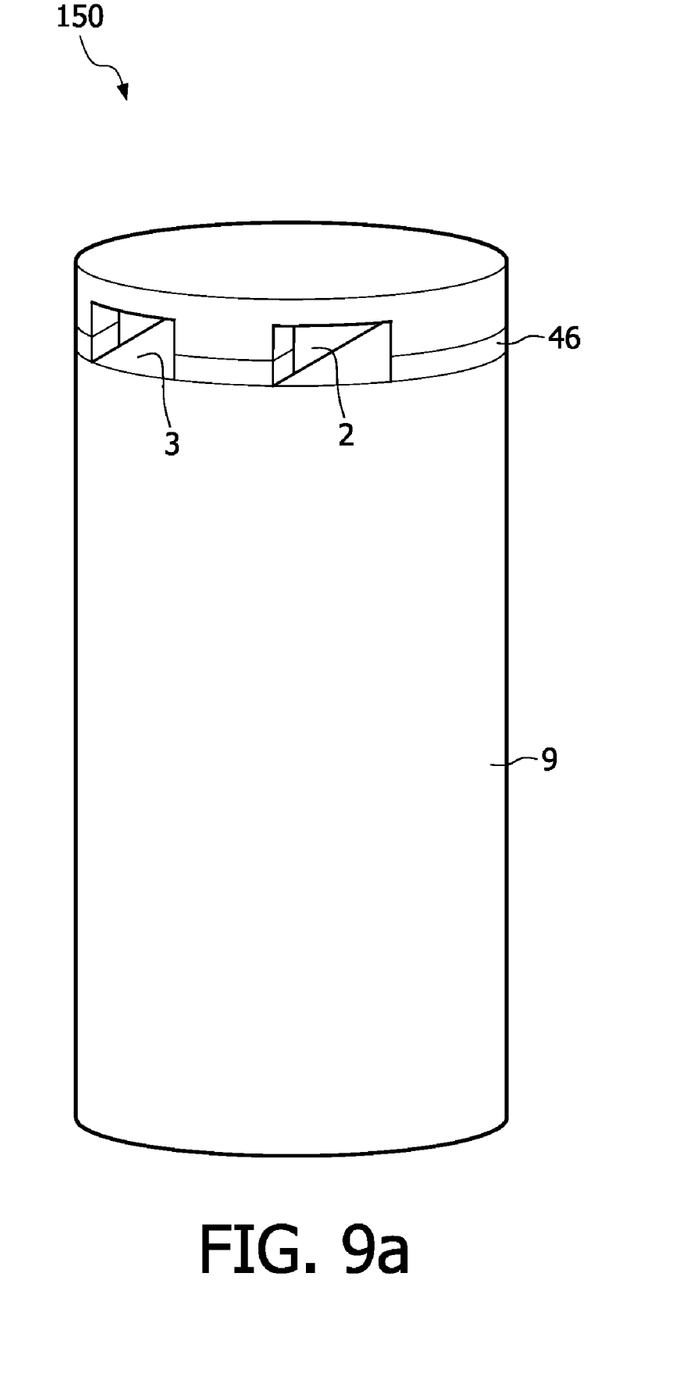
FIG. 9a is a perspective view and FIG. 9b a perspective cross-sectional view of an end part of a sensor probe according to an embodiment of the invention.
Figure 9B:
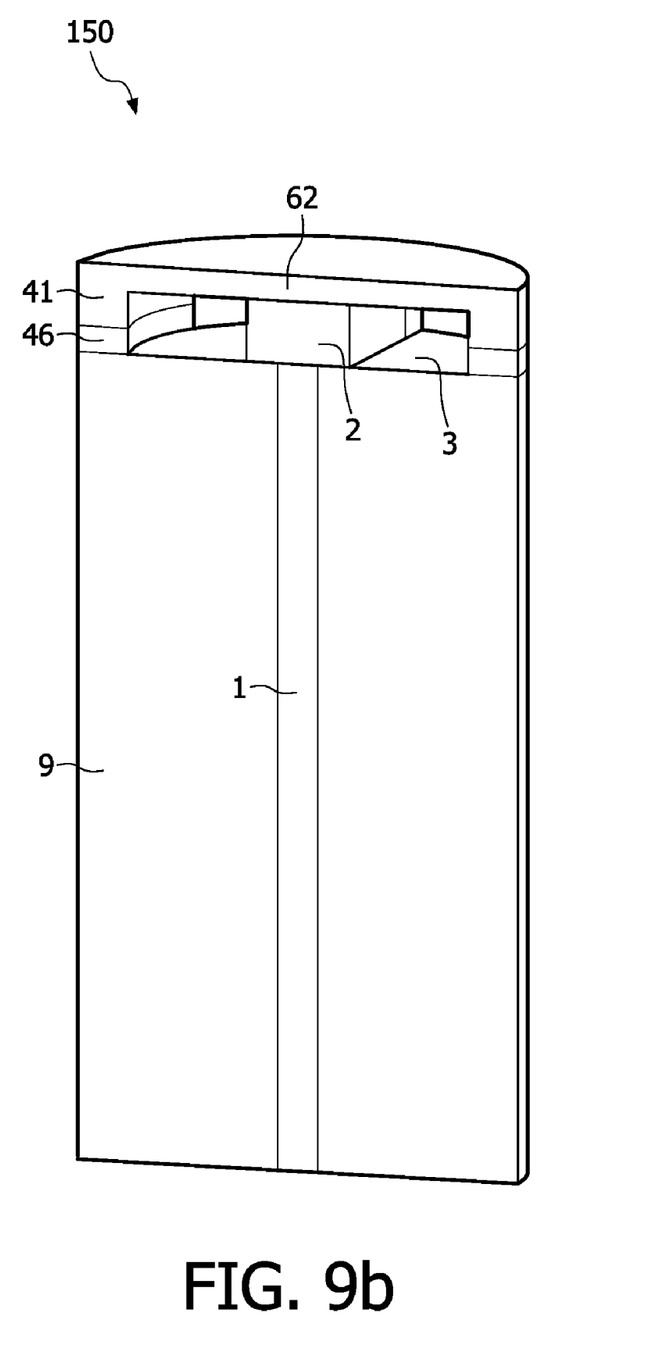

FIG. 9*a* shows a perspective view and FIG. 9*b* a perspective cross-sectional view of a sensor probe 150 according to another embodiment of the invention In this embodiment the overhanging structure does not necessarily have to be flexible, and comprises the rigid disc 62 which is supported by the rigid, partially ring-shaped, support 41 which is mounted on the end surface 3 of the elongated body 9 via the glue layer 46. The stimuli-responsive hydrogel material 2 is provided between, and adjoining, the rigid disc 62 and the end surface 3 of the elongated body 9 in the path of light that exits from the optical waveguide 1. In this embodiment the optical properties of the hydrogel material 2 will change in response to an environmental change such as, for example, a change in temperature or pH.

The optical power necessary to measure a deflection of the flexible part 22 is in the range of 0.05-0.3 mW, which is low enough not to damage blood cells, and high enough to ensure a good accuracy of the measurement. The diameter of the optical fibers 1 in the elongated cylindrical bodies 9 can be as small as 50 micrometer.

At least a part of the hydrogel material may comprise polymers that in water form a water-swollen network and/or a network of polymer chains that are water-soluble. Preferably the hydrogel material comprises in swollen state ≧50% water and/or solvent, more preferably ≧70% and most preferred ≧90%, whereby preferred solvents include organic solvents, preferably organic polar solvents and most preferred alkanols such as Ethanol, Methanol and/or (Iso-) Propanol.

The hydrogel material may have pendant moieties that are charged under physiological conditions which are very likely to be present in a device that is in direct contact with body fluid. This allows to change the osmotic pressure and therefore allows swelling.

The hydrogel material may comprise a material selected out of the group comprising poly(meth)acrylic materials, substituted vinyl materials or mixture thereof.

The hydrogel material may comprise a substituted vinyl material, preferably vinylcaprolactam and/or substituted vinylcaprolactam.

The hydrogel material may comprise a poly(meth)acrylic material made out of the polymerization of at least one (meth) acrylic monomer and at least one polyfunctional (meth) acrylic monomer. Preferably, the (meth)acrylic monomer is chosen out of the group comprising (meth)acrylamide, acrylic esters, hydroxyethyl(meth)acrylate, ethoxyethoxyethyl(meth)acrylate or mixtures thereof. The polyfunctional (meth)acrylic monomer may alternatively be a bis-(meth) acryl and/or a tri-(meth)acryl and/or a tetra-(meth)acryl and/or a penta-(meth)acryl monomer. In another alternative, the polyfunctional(meth)acrylic monomer is chosen out of the group comprising bis(meth)acrylamide, tetraethylene glycol di(meth)acrylate, triethylene glycol di(meth)acrylate, diethylene glycol di(meth)acrylate, tripropyleneglycol di(meth) acrylates, pentaerythritol tri(meth)acrylate polyethyleneglycoldi(meth)acrylate, ethoxylated bisphenol-A-di(meth) acrylate, hexanedioldi(meth)acrylate or mixtures thereof.

The hydrogel material may comprise an anionic poly (meth)acrylic material, preferably selected out of the group comprising (meth)acrylic acids, arylsulfonic acids, especially styrenesulfonic acid, itaconic acid, crotonic acid, sulfonamides or mixtures thereof, and/or a cationic poly(meth) acrylic material, preferably selected out of the group comprising vinyl pyridine, vinyl imidazole, aminoethyl (meth)acrylates or mixtures thereof, co-polymerized with at least one monomer selected out of the group neutral monomers, preferably selected out of the group vinyl acetate, hydroxyethyl (meth)acrylate(meth)acrylamide, ethoxyethoxyethyl(meth)acrylate or mixture thereof, or mixtures thereof. These co-polymers change their shape as a function of pH and can respond to an applied electrical field and/or current. Therefore these materials may be of use for a wide range of applications within the present invention.

At least one of the temperature indicators may comprise a hydrogelic material comprising monomers selected out of the group comprising poly-N-isopropylamide (PNIPAAm) and copolymers thereof with monomers selected out of the group comprising polyoxyethylene, trimethylol-propane distearate, poly-ϵ-caprolactone or mixtures thereof.

The hydrogelic material may be based on thermo-responsive monomers selected out of the group comprising N-isopropylacrylamide, di(m)ethylacrylamide, carboxylsopropylacrylamide, hydroxymethylpropylmethacrylamide, acryloylalkylpiperazine, N-vinylcaprolactam. and copolymers thereof with monomers selected out of the group hydrophilic monomers, comprising hydroxyethyl(meth)acrylate, (meth)acrylic acid, acrylamide, polyethyleneglycol(meth) acrylate, N-vinyl pyrolidone, dimethylaminopropylmethacrylamide, dimethylaminoethylacrylate, N-hydroxymethylacrylamide or mixtures thereof, and/or co-polymerized with monomers selected out of the group hydrophobic monomers, comprising (iso)butyl(meth)acrylate, methylmethacrylate, isobornyl(meth)acrylate, glycidyl methacrylate or mixtures thereof. These co-polymers are known to be thermoresponsive and therefore may be of use for a wide range of applications within the present invention.

The hydrogel material may comprise bio-responsible crosslinking moieties. Selected crosslinking pairs are (strept)

avidin-(immuno)biotin, biotin-antibiotin (Angew. Chem. Int. Ed. 2006, 45, 1446-1449), biocytin-antibiotin (Angew. Chem. Int. Ed. 2006, 45, 1446-1449), rabbit immuno globulin G—goat anti-rabbit (Nature, 399, 767), DNA-anti-sense DNA fragments. Both moieties of a selected pair are covalently bonded to the hydrogel material and can form biocrosslinks. The crosslinks are chosen such that the binding between the two moieties is in competition with the binding of one of the moieties with the analyte to be detected. The bio-responsible crosslinking moieties may be covalently bonded to functional groups incorporated in the hydrogel chains, the functional groups being selected out of the group of acrylic acid, acryloyloxy-NHS and glycidyl methacrylate. Alternatively the bio-crosslinking moieties could be attached to the hydrogel material via a ligation-chemistry route, being selected out of the group of native chemical ligation, expressed protein ligation, stauding ligation, Huisgen 2+3 cycloaddition.

In summary, a sensor probe is provided for detecting an environmental state within a bodily lumen. The sensor probe has an elongated body that comprises an optical guide having an outcoupling surface, which is part of an end surface of the elongated body, facing a reflective surface of an overhanging part, a photodetector which detects a property of light which is composed of light in the optical guide that is reflected from the outcoupling surface of the optical guide and of light in the optical guide that is reflected from the overhanging part, and a hydrogel material of which a property changes when getting into contact with an environmental material and/or when detecting an environmental change, and which is provided between the end surface of the elongated body and the overhanging part. In this way a sensor probe is provided that, because of its compactness, can be applied inside the bodily lumen for detecting and characterizing parameters that are vital indicators for the state of the human or animal body, and to which the hydrogel material is responsive.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of other elements or steps than those listed in a claim. The word "a" or "an" preceding an element does not exclude the presence of a plurality of such elements.

The invention claimed is:

1. A sensor probe for detecting an environmental state within a bodily lumen, the sensor probe comprising:
    an elongated body comprising an optical guide having an outcoupling surface, which is part of an end surface of the elongated body, facing a reflective surface of an overhanging part;
    a photodetector which detects a property of light which is composed of light in the optical guide that is reflected from the outcoupling surface of the optical guide and of light in the optical guide that is reflected from the overhanging part; and
    a hydrogel material of which a property changes when at least one of getting into contact with an environmental material and detecting an environmental change, and which is provided between the end surface of the elongated body and the overhanging part,
    wherein the overhanging part has a first portion connected to a rigid support mounted on the end surface and a second portion connected to the hydrogel material so that the overhanging part is configured to pivot at the rigid support for tilting when a volume of the hydrogel material increases in response to the at least one of the contact with the environmental material and the detecting the environmental change.

2. The sensor probe as claimed in claim 1, wherein the overhanging part is flexible.

3. The sensor probe as claimed in claim 1, wherein at least one end of the overhanging part is mounted on the end surface of the elongated body and at least partially supported by the hydrogel material.

4. The sensor probe as claimed in claim 1, wherein the overhanging part is a disc.

5. The sensor probe as claimed in claim 1, wherein the rigid support is mounted on the end surface of the elongated body outside of the outcoupling surface.

6. The sensor probe as claimed in claim 1, wherein the overhanging part comprises a fiber material at least partly coated with a reflective material on a bottom surface or on a top surface of the overhanging part.

7. The sensor probe as claimed in claim 1, further comprising processing logic for computing the environmental state from an output signal of the photodetector.

8. A medical apparatus comprising a sensor probe as claimed in claim 1.

* * * * *